United States Patent [19]

Regenass et al.

[11] B  3,994,164

[45] Nov. 30, 1976

[54] APPARATUS FOR THE DETERMINATION OF THE THERMAL EFFICIENCY OF CHEMICAL REACTIONS

[75] Inventors: Willy Regenass, Basel; Hanspeter Gfrorer, Muttenz, both of Switzerland

[73] Assignee: Ciba-Geigy Corporation, Ardsley, N.Y.

[22] Filed: June 18, 1974

[21] Appl. No.: 480,350

[44] Published under the second Trial Voluntary Protest Program on February 10, 1976 as document No. B 480,350.

[30] Foreign Application Priority Data

June 25, 1973  Germany............................ 2332135
Nov. 2, 1973  Germany............................ 2354997

[52] U.S. Cl. ............................. 73/190 R; 23/253 R
[51] Int. Cl.² .......................................... G01K 17/00
[58] Field of Search......... 73/190; 23/230 R, 253 R, 23/253 A

[56] References Cited

UNITED STATES PATENTS

| | | | |
|---|---|---|---|
| 3,080,219 | 3/1963 | Harvey, Jr. ............................ | 23/253 |
| 3,373,607 | 3/1968 | Schoenlaob............................ | 73/190 |

FOREIGN PATENTS OR APPLICATIONS

| | | | |
|---|---|---|---|
| 455,325 | 4/1966 | Switzerland............................ | 73/190 |

OTHER PUBLICATIONS

Andersen, "Polymerization Rates by Calorimetry" in Journal of Polymer Science, A-1, vol. 7, 1969, pp. 2888–2896.

*Primary Examiner*—Herbert Goldstein
*Attorney, Agent, or Firm*—Harry Falber; Karl F. Jorda

[57] ABSTRACT

An apparatus for determining the thermal efficiency of a chemical reaction wherein a reaction vessel is equipped with a double-wall jacket or shell which forms a heat exchanger, a heat transfer fluid medium is circulated so rapidly that the difference of its temperature at the inlet and at the outlet of the shell throughout the entire duration of the reaction, with the exception of possibly occurring momentary irregularities in the reaction kinetics, does not exceed 1° C. A temperature regulator is provided which is constructed as a mixture regulator and encompasses a respective container for heat transfer fluids which are hotter and colder with respect to the temperature of the heat transfer fluid which is circulated in the circulation system and each such container is operatively connected with the circulation system as a function of the reference value deviation of the temperature of the reaction mixture. Further, there is provided an apparatus for the continuous determination of the difference between the temperatures of the reaction mixture and the heat transfer fluid at a randomly selected location of the heat exchanger.

16 Claims, 4 Drawing Figures

APPARATUS FOR THE DETERMINATION OF THE THERMAL EFFICIENCY OF CHEMICAL REACTIONS

BACKGROUND OF THE INVENTION

The present invention relates to a new and improved apparatus for the determination of the thermal efficiency of a chemical reaction. In the context of this disclosure the term "thermal efficiency", or equivalent expressions, generally refer to the quantity of heat consumed or liberated in a chemical reaction.

When carrying out chemical reactions on a large scale basis as accurate as possible knowledge of their kinetic behavior is necessary. Since practically every chemical reaction is associated with a more or less large conversion of energy and the transformed quantity of heat is in a certain relationship to the reaction rate and the concentration of the reaction product it has been found that thermal analysis constitutes a practical and good expedient for obtaining information concerning the reaction kinetics of the most different reactions.

The invention of this development concerns an apparatus, generally designated as a thermal flow calorimeter, for determining the thermal efficiency of a chemical reaction, and which apparatus is of the type incorporating a reaction vessel equipped with a stirrer mechanism, a heat exchanger for influencing the temperature of the reaction mixture, the heat exchanger being located in the circulation system of a heat transfer fluid medium e.g. heat transfer liquid. Further, there are provided means for circulating the heat transfer fluid medium, measurement feelers for the temperature of the reaction mixture and the heat transfer fluid medium, and a regulation system cooperating with the measurement feelers for controlling the temperature of the reaction mixture. The regulation system embodies a reference value transmitter for the temperature of the reaction mixture and a temperature regulator which opposingly changes the temperature of the heat exchange fluid medium entering the heat exchanger for deviating the temperature of the reaction mixture by a multiple of the value of such reference value deviation.

A state-of-the-art heat flux calorimeter or thermal flow calorimeter of this type has been disclosed, by way of example, in Swiss Pat. No. 455,325. With this prior art calorimeter the heat exchanger is constructed as a pipe coil arranged within the reaction vessel. The pipe coil forms part of a circulation system in which there is circulated a suitable heat transfer medium. In the circulation system there is provided a cooling device which cools the medium down to a constant temperatuure throughout the entire reaction time. After the cooling device there is connected a heating device which heats the medium to the momentarily required temperature. By means of the heating device a regulator controls the temperature of the medium which flows into the pipe coil in such a manner that by means of the pipe coil there is always delivered or withdrawn, as the case may be, just so much heat from the reaction mixture and corresponding to the thermal efficiency that the temperature of the reaction mixture follows a preprogrammed time function. Under these conditions the quantity of heat which is consumed or liberated respectively, by the medium per unit of time through the agency of the pipe coil constitutes a measure for the thermal efficiency of the reaction. In order to determine this quantity of heat there is continually recorded the difference of the temperature of the heat transfer medium which prevails at the input and at the output of the pipe coil. Under the precondition that there prevails a constant rate of flow through the pipe coil this temperature is proportional to the quantity of heat which has been consumed or liberated, as the case may be, between the measurement points.

One of the drawbacks of this prior art thermal flow calorimeter resides in the presence of a pipe coil internally of the reaction vessel. Due to the arrangement of such pipe coil within the reaction vessel the elimination of the reaction residues which is required after each measurement is rendered extremely difficult. Although it might appear to be obvious to simply replace the reaction vessel which is equipped with the internally arranged pipe coil by means of a double-wall reaction vessel such is not possible by virtue of the specially employed measurement principle, since in the case of a double-wall reaction vessel completely different heat flow conditions prevail which cannot be so simply monitored, and which for such special measuring principle falsify the measurement results and thus render such less reliable for reaching conclusions regarding the thermal efficiency of the chemical reaction.

One of the most decisive drawbacks of the heretofore known thermal flow calorimeters resides in the stark dependency of the measuring accuracy upon the constant flow rate per unit of time of the quantity of heat transfer medium flowing through the pipe coil. It is particularly difficult with high throughput and especially in the case of non-isothermic reactions to maintain a constant throughflow rate since the viscosity characteristics of the heat transfer fluid medium markedly vary.

A further drawback of the prior art thermal flow calorimeter resides in the nature of the regulation system for the temperature of the heat transfer medium. This system functions in accordance with the throughflow principle and is much too sluggish for higher throughflow rates. Additionally, it is relatively uneconomical since owing to the series arranged cooling and heating devices it is necessary to initially cool the entire circulating medium to a constant temperature which is below the temperature which is just required and then such must be again heated to the required value.

The above-discussed drawbacks and limitations have resulted in the recognition that the heretofore known thermal flow calorimeter is not satisfactory in practice.

SUMMARY OF THE INVENTION

Accordingly it will be recognized from what has been discussed above that this particular field of technology is still in need of apparatus for determining the thermal efficiency of a chemcial reaction in a manner not associated with the aforementioned drawbacks and limitations of the prior art proposals. It is therefore a primary objective of the present invention to satisfy this need which exists in the art.

Another and more specific object of the present invention aims at the provision of an apparatus which is relatively simple in construction and extremely reliable in operation by means of which it is possible to determine the thermal efficiency of chemical reactions of random nature and under random reaction conditions, especially also larger reaction volumes, with the greatest possible resolution and accuracy.

The present invention relates to an apparatus of the previously mentioned type which is manifested by the features that the reaction vessel is equipped with a double-wall jacket or shell which forms the heat exchanger, that the heat transfer fluid medium can be circulated so rapidly that the difference of its temperature at the input and at the output of the shell throughout the entire duration of the reaction, with the exception of possibly occurring momentary irregularities in the reaction kinetics, does not exceed 1°C, that the temperature regulator is constructed as a mixture regulator and encompasses a respective container for heat transfer fluids which are hotter and colder with respect to the temperature of the heat transfer fluid which is circulated in the circulation system and each such container is operatively connected with the circulation system as a function of the reference value deviation of the temperature of the reaction mixture, and further, that there is provided an apparatus for the continuous determination of the difference between the temperatures of the reaction mixture and the heat transfer fluid or fluid medium at a randomly selected location of the heat exchanger.

The apparatus of the invention functions according to a new measurement principle. In contrast to the heretofore known apparatus the small temperature differential between the input and the output of the heat exchanger is not employed as a measurement for the thermal efficiency of the reaction, rather by sufficiently rapidly circulating the fluid medium of the circulation system such temperature differential is intentionally reduced as much as possible and therefore the difference between the temperature of the heat transfer fluid medium which is approximately equal in this way throughout the entire heat exchanger and the temperature of the reaction mixture is evaluated as a measure for the thermal efficiency of the reaction. This novel measuring principle is considerably more accurate and reliable than that employed with the previously described apparatus of the prior art. However, it cannot be realized with the heretofore known means of such apparatus, namely a pipe coil and a relatively inertia-prone temperature regulating system which functions according to the throughflow principle. The requisite precondition for such measuring principle is that there be provided a reaction vessel with a douoble-wall shell or jacket, a very rapid temperature regulation system for the heat transfer fluid medium and appropriately dimensioned circulation means in order to insure for a sufficiently rapid circulation of the fluid medium. On the other hand, the throughflow rate of the heat transfer fluid medium through the heat exchanger need not be constant.

BRIEF DESCRIPTION OF THE DRAWINGS

The invention will be better understood and objects other than set forth above, will become apparent when consideration is given to the following detailed description thereof. Such description makes reference to the annexed drawings wherein.

DETAILED DESCRIPTION OF THE PREFERRED EMBODIMENTS

Figure 1:
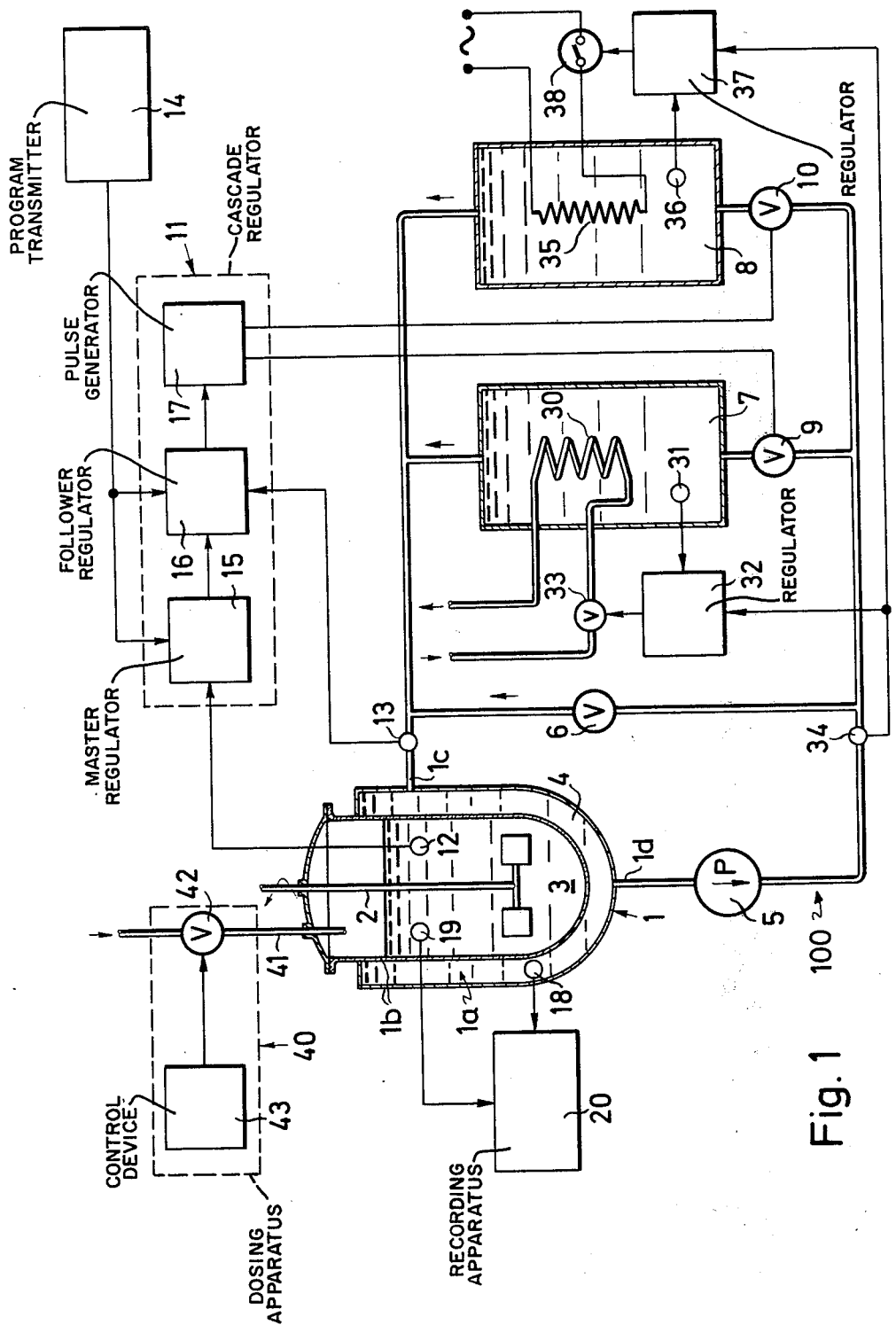
FIG. 1 is a schematic illustration of the entire arrangement of exemplary embodiment of inventive apparatus.

Describing now the drawings, in the exemplary embodiment of apparatus depicted in FIG. 1 reference numeral 1 designates a reactor or reaction vessel formed of glass and having a capacity of about 2.5 liters, this reactor being equipped with a double-wall shell of jacket. The reactor is sealed by means of any suitable cover and dimensioned such that it can withstand pressures up to about 4 atmospheres absolute (excess) pressure. A motor driven stirrer or agitator 2 extends into the interior of the reactor 1, the purpose of the stirrer 2 is to continuously mix the reaction mixture 3 which is located within the reactor so that there prevails therein an approximately homogeneous temperature distribution.

The hollow compartment or space 4 in the reactor shell, conveniently designated by reference character 1a, and formed by both of the shell walls 1b, is connected through the agency of an inlet 1c and an outlet 1d with a circulation system 100 for a heat transfer fluid medium, typically a liquid, for instance a low-viscosity silicone oil. Instead of using a liquid it is to be specifically understood that it is also however possible to use any other suitable medium. This circulation system 100 embodies the shell compartment 4, a circulation pump 5, a throttle element 6 and not particularly designated conduits or lines which operatively interconnect such components.

The circulation pump 5 possesses such a great delivery capacity that the heat transfer liquid during its passage through the hollow shell compartment 4 is neither heated or cooled, as the case may be, by more than 1°C owing to the heat exchange action with the reaction mixture. Preferably the temperature difference between the inlet 1c and the outlet 1d of the hollow shell compartment 4 should be in the order of several tenths of a degree. Such conditions are applicable for the entire course of the reaction. During sudden initiation of a reaction or during the switching-on and switching-off of the calibrated heating arrangement which is still to be described it is, however, possible that the indicated boundaries are momentarily exceeded. Such sudden briefly lasting changes of the thermal efficiency are conveniently referred to hereinafter as unstable or irregular points of the reaction kinetics irrespective of their cause. Generally, it is possible to maintain the indicated boundaries for the temperature differential in that there is circulated per minute a quantity of heat transfer liquid which corresponds approximately to three-fold to sixty-fold the volume of the shell compartment. In this way there is insured for a sufficiently rapid heat exchange with the reaction mixture in the reactor 1.

Continuing, it will be observed that connected in parallel to the throttle element 6 are a respective container or vessel 7 and 8 through the agency of a valve 9 and 10 respectively, at the circulation system 100. In relation to the quantity of liquid circulated in the circulation system 100 the container 7 contains a larger quantity of relatively cooler heat transfer fluid medium e.g. liquid, whereas the container 8 contains a relatively warmer liquid. Within the container 7 there is arranged a heat exchanger 30 through which flows any suitable coolant, for instance brine, and serving to cool the liquid flowing through the circulation system. The temperature of the liquid in the container 7 is determined by a measurement or measuring feeler 31 and delivered to a regulator 32 which controls a valve 33 arranged in the infeed conduit for the cooling liquid or coolant. In the circulation system for the heat transfer liquid there is further provided an additional measuring or measurement feeler 34 which determines the temperature prevailing at the circulation system and likewise delivers such determined temperature value to the regulator 32. Such regulator 32 actuates the valve 33 in such a manner that the difference between the temperature of the heat transfer liquid in the circulation system 100 and its temperature in the container 7 maintains an adjustable constant value. Depending upon the nature of the reaction which is to be examined the container temperature can amount to about −50°C to +180°C.

Within the container 8 there is arranged a suitable, for instance electrical heating device 35, by means of which the heat transfer liquid can be heated to a temperature in the range of about +20°C to +250°C. A temperature feeler 36 determines the container temperature and delivers such to a regulator 37 in a similar manner as for the container 7, this regulator is simultaneously also operatively connected with the temperature feeler 34 in the circulation system 100. The regulator 37 controls a switch 38 in the current circuit of the heating device 35 in analogous manner as the regulator 32.

Supposing now that, for instance, the temperature of the liquid in the circulation system should be reduced, then the valve 9 is opened and cold liquid flows out of the container 7 in a special manner still to be described into the circulation system until at that location the desired temperature has adjusted. On the other hand, for the purpose of increasing the temperature hot or warmer liquid is delivered to the circulation system from the container 8 by opening the valve 10. Owing to the relatively high delivery capacity or output of the pump 5 and the large containers for the respectively hot and cold liquid it is possible to bring the temperature of the heat transfer liquid which is located in the circulation system 100 and therefore flows through the hollow shell compartment 4 to the desired value practically without any delay in time and within a sufficiently small time span (with time-constants of about 30 seconds).

A regulation or regulator system 11 serves to control the temperature of the heat transfer liquid in the circulation system. This regulation system 11 cooperates with two temperature feelers 12 and 13 arranged within the reactor and in the circulation system or in the hollow shell compartment as well as with a program transmitter 14. This program transmitter 14 delivers the desired time course of the temperature of the reaction mixture in the reactor as a reference value. In the case of isothermic reactions this reference value of course is constant as a function of time.

This regulation system or regulator 11 is constituted by a so-called cascade regulator. It encompasses a master regulator or controller 15, a follower regulator or controller 16 and a pulse generator 17. The master regulator 15 which can possess proportional characteristics, proportional-integral characteristics or proportional-integral-differential characteristics, forms an error signal from the deviation of the actual value of the reaction temperature from its reference value. From this error signal there is formed together with the reference value of the reactor temperature the reference value for the temperature in the circulation sytem and compared with the actual value of the temperature of the circulation system. The follower regulator 16 forms an output signal from the reference value deviation of the circulation system temperature, the magnitude of this output signal determining the rate of change of the temperature of the circulation system. The follower regulator can have two point- or three point- characteristics, preferably however possesses proportional- or proportional-differential characteristics. The output signal is transformed at the pulse generator 17 into heating- or cooling control pulses which periodically open and close the valve 9 or the valve 10 respectively, depending upon whether it is desired to reduce or increase the temperature in the reactor below or above the momentary reference value. The duration and amplitude of the pulses are essentially constant. The pulse intervals between each two successive pulses are not constant, rather depend upon the magnitude of the reference value deviation of the reaction temperature and the magnitude of the output signal formed by the follower regulator. This pulse-like control of the circulation system temperature permits of the use of relatively inexpensive regulation valves, since such need only possess an open-close characteristic or function, and do not have to operate on a proportional basis.

The master regulator 15 and the follower regulator 16 are adjusted such that with a predetermined deviation of the reactor temperature from the reference value the reference temperature of the circulation system deviates by a multiple of such deviation from the momentary actual value of the circulation system temperature. A typical factor which has proven itself in practice by experience amounts to about 10; i.e. with a reference value deviation of the reactor temperature of 1°C the circulation system reference temperature is changed by 10°C. With suitable adjustment of this gain or amplification factor and the proportional band of the follower regulator it is possible to achieve the result that with thermal transformations in the reactor the temperature of the heat-transfer circulation system liquid assumes a value, within a very short period of time and practically without any overshooting, at which the thermal flow between the reactor and the circulation system is equal to the thermal efficiency in the reactor.

For determining this thermal flow or heat flux between the internal space of the reactor and the hollow shell compartment or space there are provided two further temperature feelers 18 and 19 arranged in each one of both spaces and an apparatus 20 for recording the values detected by such measurement feelers. The recording apparatus 20 plots the time-course of the difference between the reactor temperature and the circulation system temperature upon a paper strip or other suitable recording medium. At the same time there is also recorded the temperature in the reactor. The temperature difference between the reaction mixture and the circulation system liquid constitutes a measure for the thermal flow and thus for the thermal efficiency of the reaction.

For calibrating the apparatus there is provided in the internal space of the reactor an electrical heating element which has not been particularly shown. By means of this calibration heater there is delivered to the reactor during a predetermined time-span an exactly defined quantity of heat and thus there is plotted the associated heat flux or thermal flow curve which will be more fully explained hereinafter on the basis of the following example. The integral over such heat flux curve then provides a calibration factor for the apparatus.

In FIG. 1 there is additionally schematically illustrated a further advantageous auxiliary apparatus for the previously described apparatus. Such auxiliary apparatus constitutes an automatic dosing apparatus 40 by means of which solid, liquid or gaseous substances can be introduced into the reaction mixture at an exactly defined period of time or continuously in an exactly defined quantity. The dosing device or apparatus 40 encompasses a delivery or infeed line 41 which opens into the reactor, the other end of this delivery line or conduit leading to a not particularly illustrated supply container for the substance which is to be dosed. A throughflow regulator 42 is located in the delivery conduit or line 41 and such regulator is controlled by an electronic control device 43. At this control device 43 there can be conveniently adjusted the point in time and the quantity of the substance which should be supplied into the reactor.

Of course, a number of dosing devices could be provided.

Figure 4:
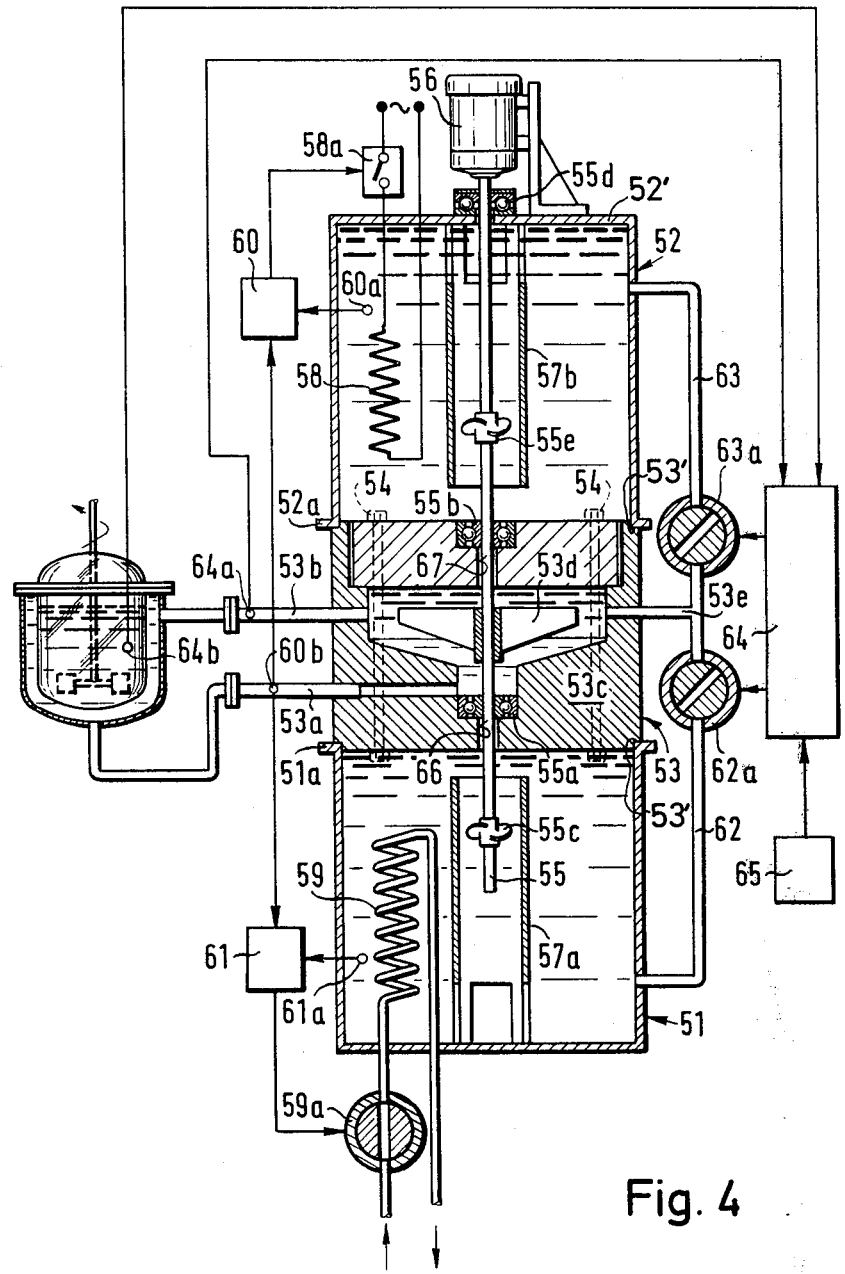
FIG. 4 illustrates in detail a variant embodiment of the apparatus depicted in FIG. 1, and partially shown in cross-sectional view.

Now in FIG. 4 there has been illustrated a particularly advantageous exemplary embodiment of the construction of a temperature regulating system for the heat transfer liquid. In this exemplary embodiment both of the containers for the heat transfer liquid and the circulation pump have been assembled together into a compact unit.

Both of the containers 51 and 52 for the heat transfer liquid are arranged in superimposed fashion, as shown, and intermediate thereof there is located the circulation pump which is shown, for instance, as a centrifugal pump 53. This pump 53 is connected through the agency of a respective suction-side connection 53a and pressure-side connection 53b with the circulation system of the heat transfer liquid.

Both of the containers 51 and 52 are of the same general construction. In the embodiment under discussion they possess a substantially cylindrical configuration with vertically extending lengthwise axes, but of course could have a different configuration, such as also a polygonal cross-sectional configuration. The housing 53c of the pump 53 is also constructed at its outer surface so as to be likewise substantially cylindrical and in this case has the same outer diamter as both of the containers 51 and 52. At the upper and lower end faces of the pump housing 53c there are suitably formed a respective annular or ring-shaped groove 53' in which there are seated the associated marginal edges of the bottomless top container 52 and the coverless lower container 51. Stated in another way both of the containers 51 and 52 are open at one respective end, but in the arrangement under discussion the end surfaces or faces of the pump housing 53c form the floor and cover of the upper container 52 and the lower container 51. The edges of the containers 51 and 52 which are seated in the annular or ring-shaped grooves 53' are equipped with a respective radially outwardly protruding flange 51a and 52a respectively. By means of these flanges both of the containers 51 and 52 are clamped together through the agency of screws 54 or equivalent fastening expedients. In this way the pump 53 is also fixedly held between both of the containers 51 and 52. Owing to the essentially equal diameter of these three superimposed and interconnected components such form a compact structural unit. To avoid any thermal losses and heat exchange between the containers via the pump the pump housing 53c is advantageously formed of a thermally insulating substance, for instance glass-fiber reinforced polytetrafluoroethylene. Additionally, this entire structural unit is enclosed by means of a not particularly illustrated envelope or shell formed of insulating material.

The pump impeller 53d of the centrifugal pump 53 is seated upon a vertical pump drive shaft 55 which is rotatably mounted at the upper and lower portion of the pump housing 53c by means of a respective radial bearing 55b and 55a. The pump shaft 55 depends downwardly into the lower container 51 and at that location carries a repulsion element, which in the illustrated embodiment comprises a propeller 55c which, during rotation of the pump shaft 55, generates an axial flow within the container 51. In similar manner the pump shaft 55 also extends upwardly and into the upper or top container 55. In this case, however, the pump shaft 55 extends through the cover 52' of such container 52 and is operatively connected with the drive shaft of a suitable drive motor 56 arranged upon such container cover 52'. An axial bearing 55d which is secured to the cover 52' secures the pump shaft 55 against axial displacement. Upon the section of the pump shaft which is located within the upper container 52 there is likewise arranged a propeller 55e or the like, and this propeller produces an axial flow at the heat transfer liquid located within the container. Owing to such flows which are produced in the containers there is obtained within such containers as uniform as possible temperature distribution. For this purpose there is also arranged in each container 51 and 52 a respective substantially cylindrical flow guide surface 57a and 57b coaxially arranged with respect to the pump shaft 55 and serving to further intensify the circulation effect.

Now in order to bring and maintain the temperature of the heat transfer medium in the upper container to the value which is required in each case for the function of the entire apparatus the container 52 is equipped with an electrical heating element 58. Furthermore, the lower container 51 is equipped with a cooling coil 59 which can be connected with any suitable and therefore not particularly illustrated source of a cooling medium or coolant. A respective regulating device 60 and 61 controls the temperature of the heat transfer liquid in the upper container 52 and the lower container 51 respectively, by actuating the electrical switch 58a and opening and closing the valve 59a respectively.

The mounting of the pump drive shaft 55 in the pump housing 53c occurs without any packing gland, in other words is not carried out so as to provide a tight seal. Therefore the internal space or compartment of the pump is continuously flow connected via the bores 66 and 67 in the pump housing, through which the pump shaft is guided, and both of the radial bearings 55a and 55b, with the lower and upper containers. The throughflow cross-sections of such connections are dimensioned such that between the inner space of the pump and the upper and lower containers there does not occur any liquid exchange brought about by convection. This can be accomplished, for instance, by carrying out an appropriately narrow dimensioning of the bores 66 and 67 or also by providing an appropriately narrow opening in the covers of the radial bearings 55a and 55b.

The pressure side of the pump 53, in other words the radially outwardly located region of the inner space of the pump, is connected via a bore in the pump housing 53c with a connection 53e at which there are connected through the agency of a branch element two conduits or lines 62 and 63, each of which is equipped with a respective shutoff or closure element 62a and 63a respectively. The conduit 62 opens into the lower portion of the lower container 51 and the conduit 63 opens into the upper portion of the upper container 52, as shown. Together with the associated container, the pump and the connection 53e, these conduits form two auxiliary or branch circulation systems for the working circulation system for the heat transfer liquid.

The mode of operation of the regulation system is as follows: During the normal condition of the system both of the valves 62a and 63a are closed. The pump 53 then circulates the heat transfer liquid only through the working circulation system. Now when the temperature in the working circulation system should increase, then, the valve 63a at the upper auxiliary or branch circulation system is opened. Consequently, a portion of the liquid which circulates in the working circulation system is branched-off through the connection or conduit 53e into the associated auxiliary or branch circulation system. This however brings about that owing to the new prevailing excess pressure in the upper container a corresponding quantity of relatively warmer liquid flows out of the upper container 52 through the radial bearing 55b into the pump 53 where at that location it admixes with the cooler circulation system liquid and finally brings about an increase of the temperature of the working circulation system.

In analogous manner for the purpose of reducing the temperature in the working circulation system the valve 62a is opened and closed. By suitably selecting the temperature differential between the liquids in the containers and in the working circulation system and by appropriately dimensioning the flow resistance in the auxiliary circulation systems it is possible to obtain an extremely rapidly reacting temperature control.

Both of the regulators 60 and 61 cooperate with a respective temperature feeler 60a and 61a in the containers 51 and 52 respectively, and a further temperature feeler 60b in the working circulation system, preferably arranged at the pump inlet, and maintain constant the difference between the temperatures of the heat exchange liquid in the working circulation system and in the containers.

Here also both of the valves 62a and 63a are controlled by means of a regulation system or regulator system, in the same manner as for the exemplary illustrated embodiment of FIG. 1, and which regulator cooperates with a respective temperature feeler 64a and 64b as well as a program transmitter 65. The temperature feeler 64a is arranged at the output-side pump connection 53b and the temperature feeler 64b is arranged in the inner space of the reactor. The regulation system 64 corresponds in its construction and in its mode of operation to the regulation system 11 of the embodiment of FIG. 1.

The temperature control unit for the heat transfer liquid as illustrated in FIG. 4 is extremely simple in construction and therefore relatively inexpensive. In particular it requires only a single drive motor for the circulation pump and both of the propellers in the containers. The individual components including the pipe conduits can be limited to a minimum and the pipe conduits also can be designed of extremely short construction. The apparatus is very compact and constitutes a space-saving unit owing to the direct connection of both containers with the pump into a unitary assembly. Due to the unique arrangement of the pump between both of the containers it is possible to save at least two pipe conduits and in particular to avoid having to use a relatively inexpensive sealed mounting arrangement for the pump shaft in the pump housing. The arrangement of the containers above one another and the pump drive motor upon the upper container also renders possible a glandless and therefore inexpensive mounting of the pump shaft at the cover of such container.

There will now be described hereinafter the functioning of the equipment illustrated in FIG. 1 on the basis of the examination of the isomerism of trimethylphosphite by way of example. The reaction proceeds according to the equation:

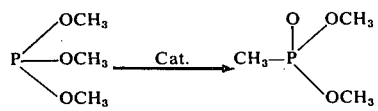

If such reactions run out of control then the reaction mixture heats up very intensely and thus attains high vapor pressures. The pressure increase occurs so rapidly that there cannot be realized a stabilizing boiling, rather than a foaming of the reaction mass which can even bring about bursting of an open reactor or reaction vessel.

Elementary analysis of such reactions have shown that they are increasingly more dangerous the quicker that they proceed. However, for production reasons there is an interest to have these reactions occur with as great as possible reaction rates. In order to clarify the question what reaction rate is permissible within the prevailing safety regulations and under what reaction conditions such rate can be realized there is required a model of the reaction kinetics. To this end there is provided a mathematical model with a number of variable parameters and such parameters are varied by means of a computer in such a manner until the mathematical model coincides with the experimental data.

Figure 2:
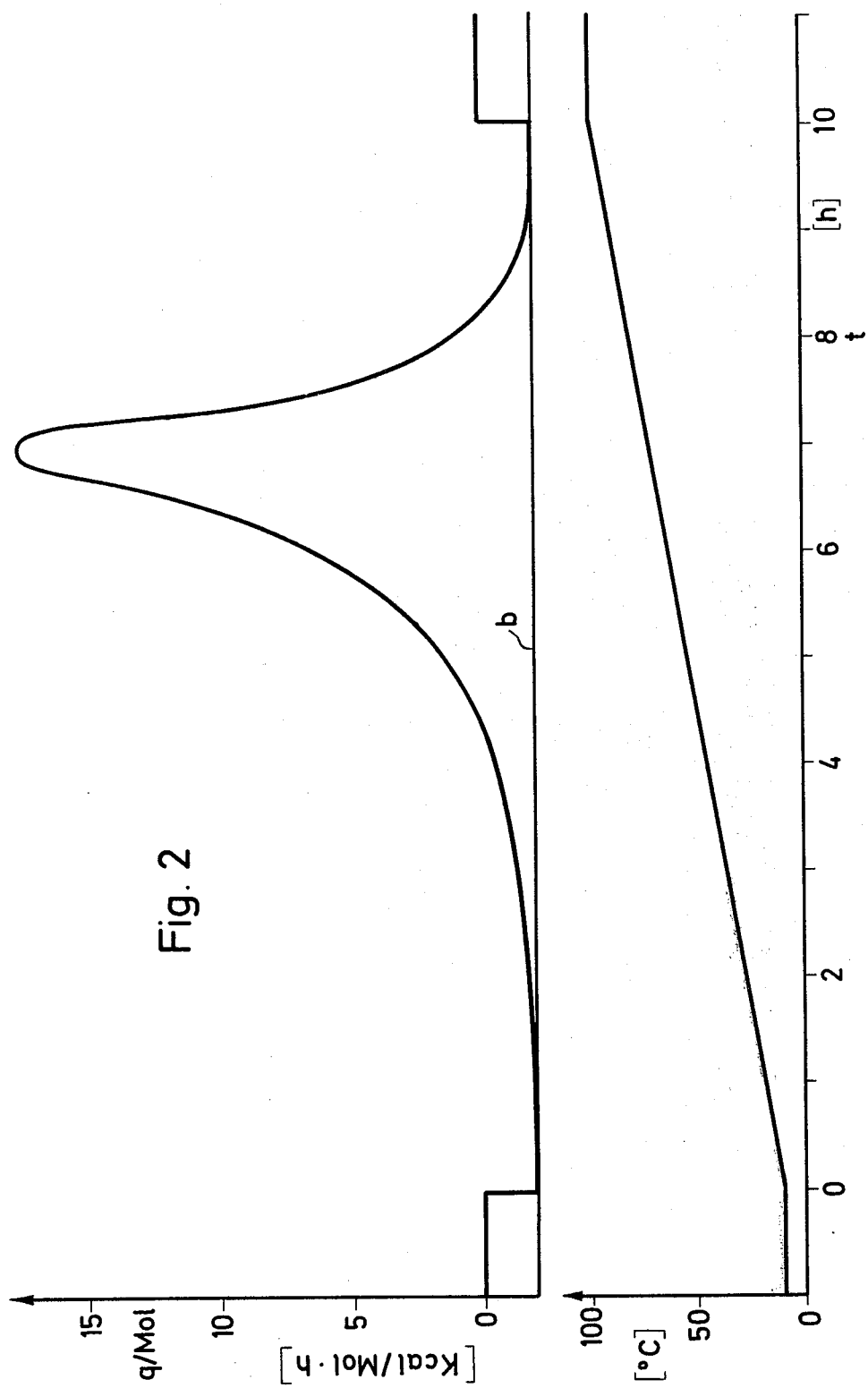
FIG. 2 graphically illustrates an example of a heat flux or thermal flow curve of a temperature-programmed course of reaction determined with such apparatus.
Figure 3:
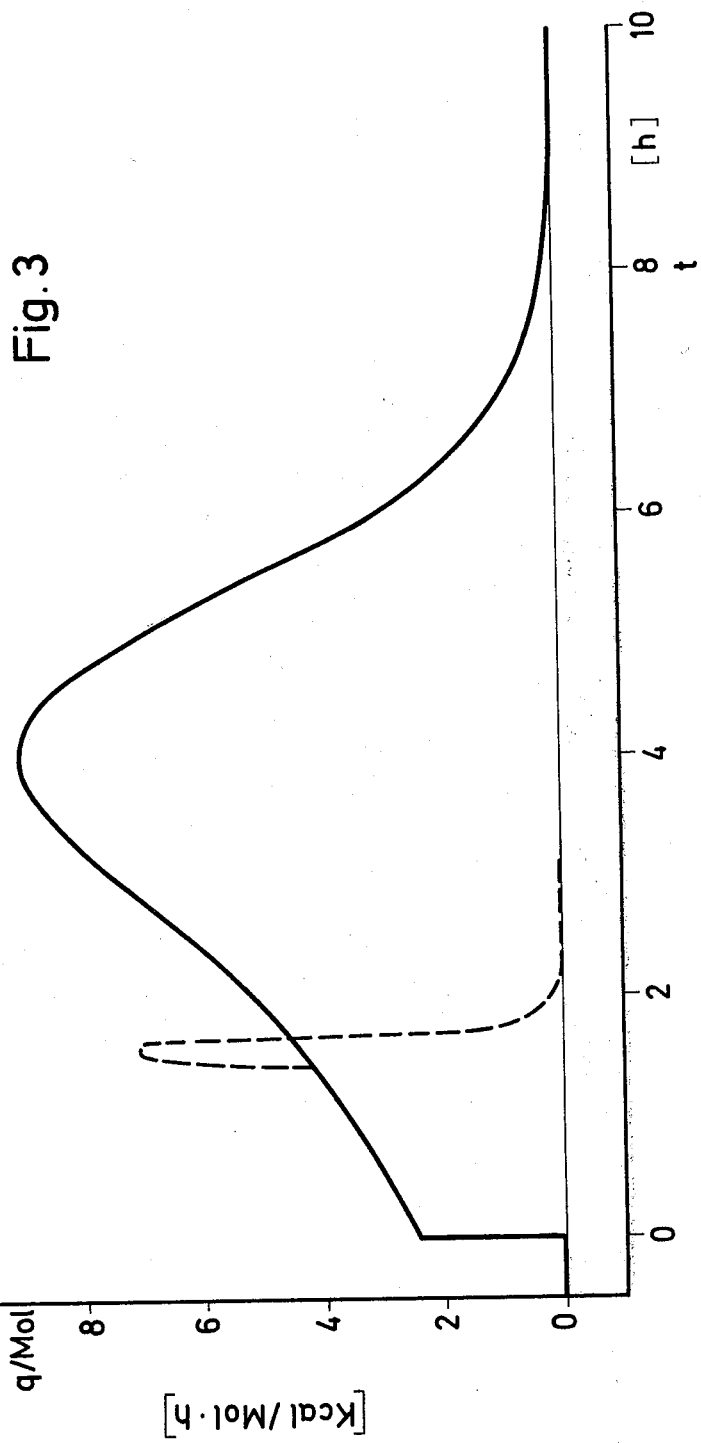
FIG. 3 is a graph illustrating an example for the thermal flow curve of an isothermic reaction.

FIG. 2 illustrates the results of a temperature-programmed thermal flow experiment, and FIG. 3 that of an isothermal flow experiment.

For the practical performance of the temperature-programmed thermal flow experiment the reaction constituents are admixed with one another in a cold condition. Thereafter the reaction mixture is carefully heated in that the program transmitter 14 is set to a linear temperature increase of about 8°C per hour. The increase of the temperature in the reactor is illustrated at the lower portion of the diagram of FIG. 2. The regulator 11 then controls the circulation system temperature such that the temperature in the reaction vessel assumes the course prescribed by the program transmitter.

As readily recognized from the showing of FIG. 2 the heat flux or thermal flow curve at the start of the temperature increase has a sudden negative drop or jump. This is caused by the fact that the temperature of the heat transfer liquid in the circulation system must be greater by a certain amount than the temperature of the reaction mixture if this temperature should follow the desired program. From the magnitude of this temperature jump towards the negative it is possible to determine the specific heat of the reaction mixture.

Owing to the increasing temperature in the reactor the reaction gradually begins to start and thus releases heat which brings about that the reaction temperature tends to increase beyond the reference temperataure prescribed by the program transmitter. This attempt on the part of the reaction temperature to exceed the prescribed reference temperature is immediately counteracted by the regulator in that it reduces by an appropriate value the temperature of the heat transfer liquid. The difference between the reactor temperature and the circulation system temperature results in the heat flux curve illustrated in FIG. 2. The ordinate of such diagram has already been calculated in Kcal per Mol.

As recognized by referring to FIG. 2 the reaction rate, which is a measure of the heat flux, at the start increases relatively slowly and then very rapidly to a maximum value and finally again drops back to null owing to the increasing throughput. From this point in time any further heating-up of the reaction mixture is no longer sensible because now the reactor temperature is maintained constant. In so doing the thermal flow curve of course again makes an upward jump at the value null and then extends horizontally, as shown.

The thin horizontal full-line $b$ shown in the drawing of FIG. 2 is designated as the base line. The momentary thermal efficiency of the reaction can be ascertained from the vertical spacing of the corresponding point along the thermal flow curve from such base line. The surface which the thermal flow curve encloses together with the base line corresponds to the total heat transformation of the reaction.

In order to carry out the isothermal experiment (FIG. 3) initially the mixture, without any catalyst, is brought to the reaction temperature, then at the point in time designated by reference character O there is added the catalyst ($CH_3J$). The full line illustrates the undisturbed isothermal reaction course. The broken line curve illustrates the reaction course after the addition of an inhibiter. The inhibiter (triethylamine) reacts in an exothermal very rapid reaction with the catalyst and thus brings the reaction to standstill.

The last experiment particularly accentuates the advantages and possibilities of the previously described exemplary embodiments of equipment. It shows that with the inventive equipment it is possible to better and more clearly detect the special particular dangers which inherently reside in the kinetics of the isomerism of trimethylphosphite than with the classical techniques. On the other hand, it clearly demonstrates in a particularly impressive manner the important significance of the possibility of being able to undertake manipulations at the reaction mixture during the measurements.

Of course, with the previously described exemplary embodiments of equipment one is not bound to initiating the reaction by heating or by a single or one-shot addition of a catalyst. For instance, it is possible to continuously introduce into the reactor by means of the automatic dosing devices a reaction component during the isothermal or temperature-programmed reaction course.

The recording device of course is not limited to a paper strip-plotting device, rather there can be used any suitable device by means of which it is possible to record or retain the temperature values determined by the measurement feelers. For instance the recording device can be a storage from which the stored information is delivered to a computer which, on the basis of this information, directly calculates an appropriate theoretical kinetic model of the reaction.

With the previously described equipment, among other things, the following advantages are particularly worthy of comment.

a. The possibility of examining technical, concentrated exothermic and endothermic reaction systems under the conditions which approximate those prevailing during production;

b. Close actual surface-volume conditions of the examined reaction mixture;

c. The possibility of carrying out isothermal, temperature-programmed and if necessary also adiabatic experiments;

d. The possibility of interceding in the course of the reaction by dosing-in gaseous, solid and liquid reagents according to adjustable dosing programs;

e. The possibility of determining the theoretical kinetics through a number of few isothermal and temperature-programmed experiments;

f. When using glass reactors there is the possibility of visually observing the reaction course (phase-, modification-, color- and viscosity changes of the reaction mixture); and g. When using appropriately constructed metallic reactors there is the possibility of examining high-pressure reactions with the same basic equipment (heat exchanger system, regulator system).

While there is shown and described present preferred embodiments of the invention, it is to be distinctly understood that the invention is not limited thereto but may be otherwise variously emobided and practiced within the scope of the following claims. ACCORDINGLY,

What is claimed is:

1. In an apparatus for determining the thermal efficiency of a chemical reaction, comprising a reaction vessel equippeed with agitation means, a circulation system for a heat transfer fluid medium in communication with said reaction vessel, a heat exchanger for influencing the temperature of the reaction mixture in contact with said reaction vessel and positioned in said circulation system, means positioned in said circulation system for circulating the heat transfer fluid medium, measuring feeler means positioned, respectively, in said reaction vessel and said circulation system for determining the temperature of the reaction mixture and the heat transfer fluid medium, a regulating system cooperatingly connected to said measuring feeler means for controlling the temperature of the reaction mixture, said regulating system including a reference value transmitter for the temperature of the rection mixture and a temperature regulator for opposingly changing the temperature of the heat transfer fluid medium entering the heat exchanger by a multiple of the amount of the reference value deviation from an instantaneous value to establish a set point for the heat transfer fluid, the improvement comprising the reaction vessel being equipped with a double-wall shell constituting said heat exchanger, said shell having inlet and outlet means; the means for circulating the heat transfer fluid medium comprising a circulating mechanism for circulating the heat transfer medium so rapidly that the difference of its temperature at the inlet and at the outlet of said shell over the entire reaction duration, except during possibly occurring momentary unstable points in the reaction kinetics, does not exceed 1°C; the temperature regulator comprising a mixing regulator having a first container for a heat transfer fluid medium which is warmer than the temperature of the heat transfer fluid medium circulating in the circulation system and a second container for a heat transfer medium which is colder than the temperature of the heat transfer fluid medium circulated in the circulation system, means responding to said feeler means and connected to said circulation system for selectively discharging said warmer and colder heat transfer fluid mediums into the circulation system as a function of the reference value deviation of the temperature of the reaction mixture and as a function of the deviation of the temperature of the heat transfer medium from said set point; and means for the continuous determination of the difference between the temperatures of the reaction mixture and the heat transfer fluid medium at a random location of the heat exchanger, said temperature difference being representative of the thermal efficiency to be measured.

2. The apparatus as defined in claim 1, wherein each container has operatively associated therewith a regulator which maintains at least approximately constant the temperature difference between the heat transfer fluid medium in the associated container and in the circulation system.

3. The apparatus as defined in claim 2, wherein said means for selectively connecting the containers with the circulation system comprises a respective open-close valve provided for each container, said valves being controlled by the temperature regulator for the heat transfer fluid medium circulated in the circulation system, the duration of the opening phases of said valves being constant and the closed phases of the valves being variable as function of the reference value deviation of the temperature of the reaction mixture and as a function of the deviation of the temperature of the heat transfer fluid medium from said set point.

4. The apparatus as defined in claim 1, wherein said circulating mechanism circulates said heat transfer fluid medium in the circulation system at a rate per minute corresponding to at least three times the volume of the heat exchanger.

5. The apparatus as defined in claim 4, wherein said circulation rate per minute amounts to at least 60 times the volume of the heat exchanger.

6. The apparatus as defined in claim 1, further including means operatively connected to said reaction vessel for the introduction of at least one substance into the reaction vessel as a function of time and quantity.

7. The apparatus as defined in claim 1, wherein the circulation mechanism comprises a centrifugal pump arranged between both containers, said centrifugal pump having a pump shaft which extends into one of the containers and piercingly extends completely through the other container, a drive motor arranged externally of said other container, said pump shaft being connected with said drive motor, at least one respective propeller-like element arranged at respective portions of the pump shaft located within the containers for producing a circulatory movement within each associated container.

8. The apparatus as defined in claim 7, further including a respective valve provided for each container, both of the containers while interposing a respective one of said valves being connected in parallel with said centrifugal pump.

9. The apparatus as defined in claim 8, wherein said centrifugal pump includes a pump housing having throughpassages for said pump shaft, said pump shaft extending through said throughpassages and being mounted without any seals in the pump housing, said centrifugal pump having a suction side and a pressure side, and wherein the containers are flow connected with the suction side of the centrifugal pump via said throughpassages of the pump shaft.

10. The apparatus as defined in claim 9, wherein the pressure side of the centrifugal pump is connected with the containers by a branched pipe conduit and at each branch of said branched pipe conduit there is arranged one of said valves.

11. The apparatus as defined in claim 9, wherein the pump housing embodies a block of at least approximately the same outer cross-sectional configuration as that of said containers, and means for interconnecting the containers and the pump housing into a unitary assembly.

12. The apparatus as defined in claim 11, wherein the pump housing is fabricated from a heat insulating material.

13. The apparatus as defined in claim 12, wherein the heat insulating material is formed of plastic.

14. The apparatus as defined in claim 7, wherein the containers are arranged above one another in superimposed fashion defining an upper container and a lower container, and the drive motor is mounted at the upper container.

15. The apparatus as defined in claim 7, further including substantially cylindrical guide flow surface means which coaxially enclose the pump shaft and the propeller-like elements arranged within the containers.

16. The apparatus as defined in claim 7, wherein one of the containers is equipped with electrical heating means and the other container with a heat exchanger.

* * * * *